(12) United States Patent
Fortt et al.

(10) Patent No.: US 8,664,617 B2
(45) Date of Patent: Mar. 4, 2014

(54) MULTI-STREAM SPECTROPHOTOMETER MODULE

(75) Inventors: Robin Fortt, London (GB); Colin Steel, London (GB); Victor D. Samper, Garching b. Munchen (DE); Marko Baller, Munich (DE)

(73) Assignees: GE Healthcare UK Limited, Little Chalfont (GB); General Electric Company, Schenectady, NY (US)

( * ) Notice: Subject to any disclaimer, the term of this patent is extended or adjusted under 35 U.S.C. 154(b) by 0 days.

(21) Appl. No.: 13/499,757

(22) PCT Filed: Oct. 8, 2010

(86) PCT No.: PCT/US2010/051964
§ 371 (c)(1),
(2), (4) Date: Apr. 2, 2012

(87) PCT Pub. No.: WO2011/044453
PCT Pub. Date: Apr. 14, 2011

(65) Prior Publication Data
US 2012/0207650 A1    Aug. 16, 2012

Related U.S. Application Data

(60) Provisional application No. 61/249,707, filed on Oct. 8, 2009.

(51) Int. Cl.
*G01J 1/42*    (2006.01)
(52) U.S. Cl.
USPC ............................................. 250/373

(58) Field of Classification Search
USPC ............................................. 250/373
See application file for complete search history.

(56) References Cited

U.S. PATENT DOCUMENTS

| 4,591,721 | A | * | 5/1986 | Wong ............................ 250/373 |
| 5,422,068 | A | * | 6/1995 | Shalaby et al. ................ 422/22 |
| 5,432,096 | A | | 7/1995 | Zhu |
| 2001/0035947 | A1 | | 11/2001 | Fry et al. |
| 2007/0121114 | A1 | * | 5/2007 | Berry et al. .................... 356/442 |
| 2007/0182965 | A1 | | 8/2007 | Kamlet et al. |
| 2008/0135484 | A1 | | 6/2008 | Hammer |

OTHER PUBLICATIONS

PCT/US2010/051964 ISRWO DTED May 25, 2011.

* cited by examiner

*Primary Examiner* — Kiho Kim (57) ABSTRACT

A multi-stream optical interrogation flow cell (60) for a radiopharmaceutical includes a multiple flow cell body (10a-f) defining a first elongate fluid flowpath (A1-6;B1-6) therethrough for individually conducting a radiopharmaceutical therethrough in fluid isolation from other of the flow cell bodies. Each flow cell body further defines a first and second aligned UV transparent optical guides (36,38) and a first interrogation passageway (26a-f) extending between the first and second optical guides such that a portion of the elongate first fluid flowpath intersects the interrogation passageway such that the radiopharmaceutical flows in between the first and second optical guides. The first and second interrogation passageways of all of the flow cell bodies are optically aligned so that a single interrogation beam is able to extend through each of the interrogation passageways.

18 Claims, 6 Drawing Sheets

MULTI-STREAM SPECTROPHOTOMETER MODULE

This application is a filing under 35 U.S.C. 371 of international application number PCT/US2010/051964, filed Oct. 8, 2010, which claims priority to U.S. application No. 61/249,707 filed Oct. 8, 2009, the entire disclosure of which is hereby incorporated by reference.

FIELD OF THE INVENTION

The present invention is directed to the field of radiopharmaceutical preparation or purification. More specifically, the present invention is directed to a multi-stream optical interrogation module.

BACKGROUND OF THE INVENTION

Positron emission tomography works by measuring the spatial distribution of a specific molecular imaging probe, a so called PET-tracer, in the body of the patient. The tracer is injected in trace amounts into the patient and has the ability to specifically bind to tissue or be enriched in certain areas because of their specific involvement in biological processes. PET-tracers are used in cancer diagnosis and therapy control.

Figure 1:
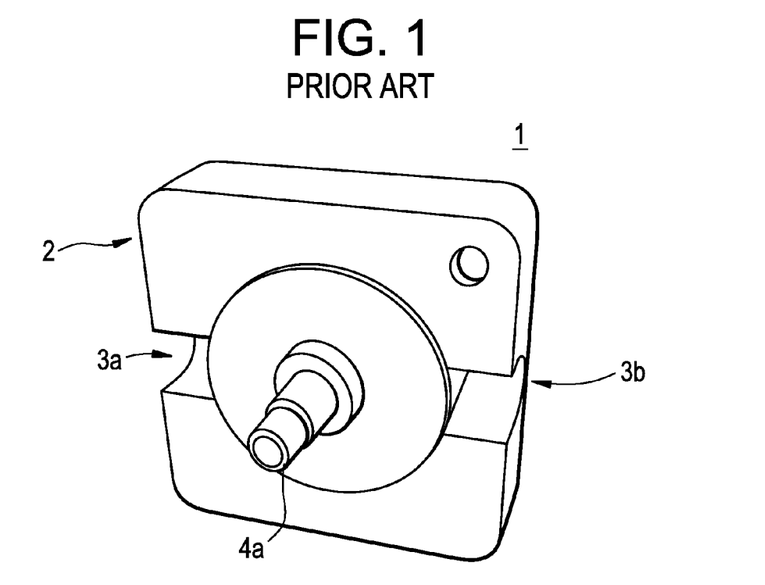
FIG. 1 depicts an individual optical flow cell of the prior art.
Figure 2:
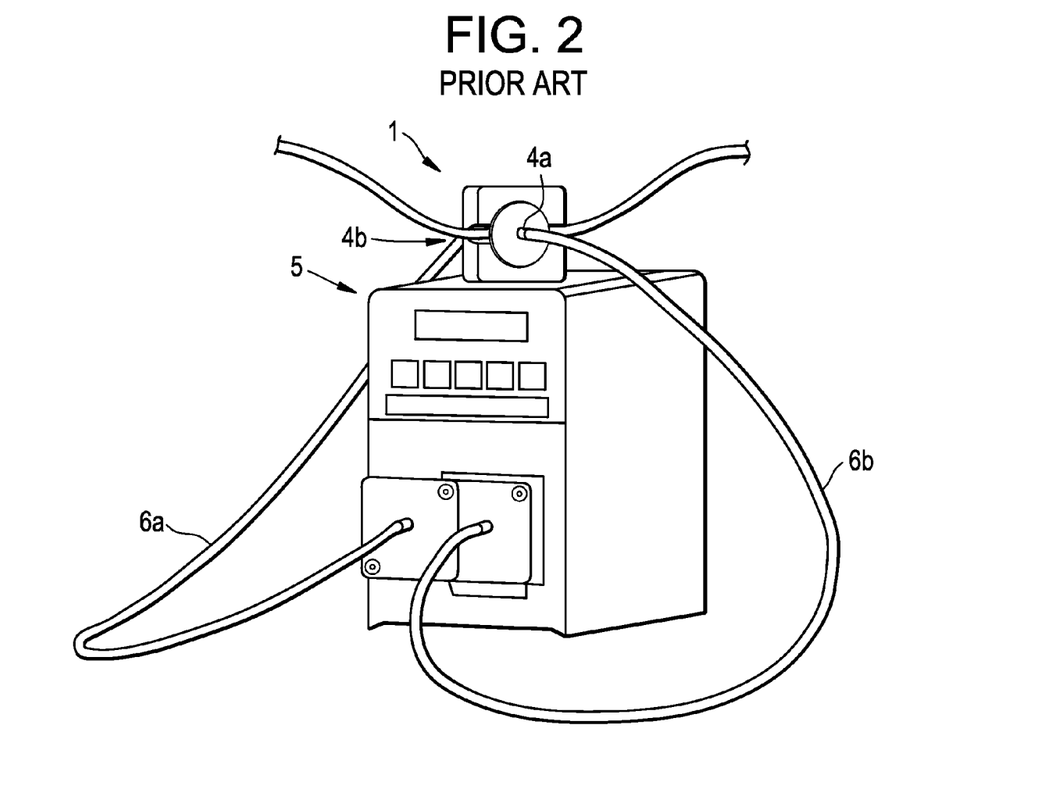
FIG. 2 depicts a photospectrometer connected to a flow cell of the prior art.

In current PET tracer synthesis protocols, the lack of space within hot cell compartments is a significant limitation on tracer production and purification. The drive to increase production capacity drives the need for smaller and higher-capacity devices. One important step in the process is the final purification of the radiopharmaceutical compound. In the general case of PET tracer synthesis, final purification is performed by liquid chromatography, such as high-pressure liquid chromatography (HPLC), operating at about 300 bar back-pressure within the column. With reference to FIGS. 1 and 2, the purified compound is then detected via an optical flow cell 1 for ultraviolet light absorption and a gamma detector 5 for the activity. Flow cell 1 includes a housing 2 fluid input port 3a and output port 3b in fluid communication with the HPLC column so that output from the column flows through the flow cell body. Flow cell 1 also includes opposed optical ports 4a (shown) and 4b (hidden) in registry across a portion of the flow channel in housing 2. Cables 6a and 6b extend between the opposed optical ports to detector 5 so that detector 5 may optically interrogate fluid flowing through flow cell 1. In order to avoid cross contamination between runs, each HPLC column has an associated pump mechanism, UV-flow cell, and gamma detector. After each use, the separation system i.e. the HPLC column and flow cell, are rinsed by solvents to clean the system from chemicals and minimizing the residual activity as much as possible. These systems must also be disinfected at regular intervals.

Commercially-available multi-stream UV-Vis spectrometers are primarily focused on the high throughput production analyzing multiple chromatography streams simultaneously with multiple interrogation beams which are each dedicated to a single stream. However, not only are these commercial multi-channel systems large and expensive compared to single channel spectrometers, they are far more powerful than is required. Because while cartridge-based automated synthesis system allows the production of multiple different samples, the synthesizer produces each sample sequentially and thus only a single synthesis and analysis may be, or is even required to be, performed at any one time.

There is therefore a need for simplified components used with the multiple HPLC columns. There is a need to these components to minimize the space required in the hot cells.

DETAILED DESCRIPTION OF THE PREFERRED EMBODIMENT

In view of the needs of the art, the present invention provides a multi-stream spectrophotometer, or interrogation, module. The interrogation module is desirably used with a multi-stream HPLC system within a hot cell. The interrogation module includes a plurality of independent flow cells of the present invention arranged for interrogation by a single UV source. The independent flow cells of the present invention incorporate a modular design allowing multiple flow cells to be arrayed in optical communication. That is, the interrogation channels of the flow cells is are linearly-aligned so that a single interrogation beam shines through all of the interrogation channels. As only a single flow cell will be interrogated at any given time, only a single interrogation beam is required for all of the arrayed flow cells.

Therefore, the present invention provides an interrogation module providing a multi-stream flow channel array. The system consists of a flow channel array and commercially available spectrometer and fiber optic components adapted for serial mechanical and optical connection. The flow channel array will be located within a hot cell, connected via the fiber optic components to the spectrometer which is located outside of the hot cell.

The present invention thus provides a multi-stream optical flow cell in a compact and modular form. Component flow cells of the present invention may be assembled to provide a selectable capacity, depending on the number of flow lines to accommodate. Fewer connections are thus required between subsequent synthesis runs and the present invention removes the possibility of incorrect connection between the flow cells and HPLC column. The multi-stream optical interrogation flow cells of the present invention provide for transmission and measurement of the ultra-violet (UV), visible, or infrared (IR) spectra. Additionally, the multi-stream optical flow cell of the present invention provides for multiple applications, e.g., radio-synthesis, process analysis, quality control, method development, etc. The multi-stream optical flow cell may be made from suitable materials so as to be either reusable or as to be a low-cost disposable component obviating the need for periodic cleaning and maintenance. Additionally, the present invention is suitable for HIL GMP requirements.

The flow cells of the present invention can have applications in process control and quality control. Depending on the interrogation wavelength, the optical flow cell can utilize windows formed from the miniature synthesizer bulk material e.g. polymer, or can integrate materials such as quartz for use over a broader range of wavelengths. Identification and verification of the product peak after chromatographic purification of synthesized tracers, is often performed by analyzing the output from the separation media, within a target time window, by a combination of a gamma and ultraviolet absorbance measurements. Moreover, as for product peak identification after purification, an ultraviolet flow cell can also be utilized for quality control or process control after reformulation.

The flow cell of the present invention should be made from material that are suitable for sterilization (gamma, Ethylene Oxide or steam), in order to ensure sterility of the purified product. Suitable materials include stainless steel and optical-quality glasses and polymers. The flow cell should be able to handle an appropriate clean room class to ensure bioburden level per system below 200 cfu.

Alternatively, the flow cells of the present invention may be constructed using, by way of illustration and not of limitation, only optical rods (made of for example quartz or UV transparent or semitransparent polymers such as polymethylmetacrylate (PMMA) and a polymer body, (made of for example Cyclic Olefin Copolymer (COC), Polyetherimide (also called as Ultem®), Polypropylene (PP), Polyethylene (PE), Polyetheretherketone (Peek™), Polymethylpentene (TPX), polyvinyldienefluorine (PVDF), Polytertrafluorethylene (PTFE), Polyphthalazinoneethersulfone (PPES), Polyphthalamide (PPA), Liquid Cristal polymer (LCP), Polyphenylenesulfide (PPS), Polyethersulfone (also called Radel®), Polycarbonate (PC), fluoroethylkenepolymer (FEP)), or other materials suitable for the purpose. The rods are aligned coaxially and secured in a polymer block. Their opposing end faces are separated by a short length of empty space inside the polymer block. The opposing end faces of the rods form the internal walls at the ends of a chamber through which the fluid sample flows. By this means UV absorption can be measured across the fluid guided into the chamber between the quartz rods. An inlet and outlet channel are formed in the polymer block for passing fluids into and out of the measuring chamber. Because the flow cell may consist of only simple quartz rods and an injection molded piece of polymer, the costs of such cells are low and manufacturing is straightforward, thereby enabling disposability. The quartz rods make it possible to measure absorbance into the UV range where many other materials become highly absorbing. This maintains the useful optical wavelength range of a classical flow cell, but dramatically reduces the cost.

Consequently, a spectrometer used in combination with such automated synthesizer requires only a single UV source and detector and only dictates that the fluid paths must be kept separate. This can be achieved simply by utilizing a sequential array of flow cells with a common light path through each cell. The use of single channel UV, visible or IR spectrometer in conjunction with a single data processing unit and multiple flow cells would allow the analysis of a number of products to be obtained sequentially without significant increase of the overall size of the detection system. Emission, collection and detection may be achieved via optical fibres to/from the flow cell array thus allowing the bulk of the detector electronics to be housed outside of a lead shielded enclosure.

The array of flow cells can be achieved in a number of different ways. For example, commercially available flow cells can be arrayed sequentially using spacers that are opaque to UV and visible light in order to align the optical components of the flow cell and prevent possible light contamination of the adsorption signal. Connection of the array to the spectrometer can then be achieved by the use of commercially available fiber optic components as shown above.

Alternatively, a disposable flow cell or cells may be used comparable to that of a cassette based automated synthesis platforms. These flow cells may consist of a single moulding incorporation multiple flow channels and connectors or several separate cells with individual connection points. These disposable cells would subsequently be placed in a device to hold the cells in proper optical alignment between the light source and detector and provide connection for the fiber optic components.

The interrogation module of the present invention may be employed with a multi-stream purification system, such as that disclosed in commonly-owned patent application, attorney docket no. PZ1063, filed on even date herewith, entitled "MULTI-STREAM HIGH-PRESSURE LIQUID CHROMATOGRAPHY MODULE". Delivery of multiple $^{18}$F radiotracers from a radiosynthesis platform can thus be directed to a GMP-compliant multi-compound radioHPLC system which utilizes a combination of compound-dedicated hardware and line clearance between differing radiosyntheses. The present invention enables compound-dedicated flowcells to be utilized. The prior art employs a dedicated multi-channel spectrometer which contains multiple flow cells, light sources and detectors in one assembly, each being controlled and analyzed using a single data processing unit and interface. These prior art systems utilizing multiple UV flowcells require multiple connections and disconnections between the flow cells and the appropriate HPLC columns. Each of these connection and disconnection operations is open to user error leading to use of the incorrect flow cell with a particular synthesis and increases the number of connections that need to be made increasing the likelihood of a leak or the waste-loss of the output from the synthesizer when the connections are improperly performed.

However, with the present invention, each flow cell is dedicated to a particular synthesis and HPLC column, and thus no cross contamination can occur. Additionally as the flow cell does not require being changed at any point after the validation of the system, errors due to incorrect connection of the flow cell to the column are obviated.

Figure 3:
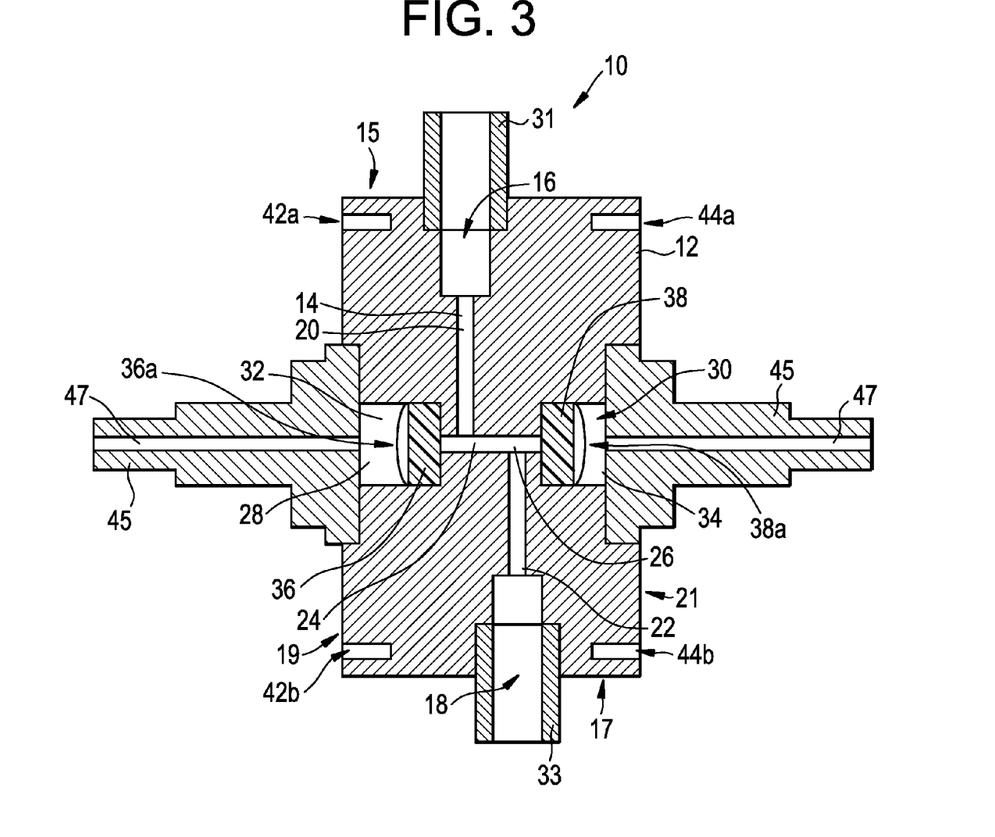
FIG. 3 depicts, in cross-section, an optical flow cell of the present invention.

Referring now to FIG. 3, the present invention provides a flow cell 10. Flow cell 10 includes a cell body 12 which defines an elongate fluid channel 14 therethrough. Cell body 12 is desirably formed from a suitable material for radiopharmaceutical production and handling. Cell body 12 includes a first face 15 which defines a fluid inlet port 16 and a second face 17 which defines a fluid exit port 18 such that fluid channel 14 extends in fluid communication therebetween. Cell body 12 defines fluid channel 14 to include a fluid entry segment 20 proximate inlet port 16 and a fluid exit segment 22 proximate fluid exit port 18. Fluid interrogation segment 24 extends in fluid communication between fluid entry segment 20 and fluid exit segment 22.

Cell body 12 also includes a third face 19 that defines a first optical port 28 and an opposed fourth face 21 which defines a second optical port 30 and an elongate optical channel 26 extending between. Optical channel 26 includes a first optical segment 32 in optical-communication with first optical port 28 and a second optical segment 34 in optical-communication with second optical port 30. First optical segment 32 and second optical segment 34 are coaxially-aligned across fluid interrogation segment 24 of fluid channel 14. First optical segment 32 accommodates a transparent first optical guide 36 therein so as to fluidly-seal optical segment 32 so that no fluid leaks from interrogation segment 24 thereinto. Similarly, second optical segment 34 accommodates a transparent second optical guide 38 therein so as to fluidly-seal optical segment 34 so that no fluid leaks from interrogation segment 24 thereinto. First and second optical guides 36 and 38 are desirably formed from optically-transparent lenses or guiding rods or fibers. In operation, an interrogation light beam is directed into cell body 12 through first optical guide 36, through interrogation channel 24 of fluid channel 14, and then out cell body 12 through second optical guide 38. Optical guides 36 and 38 provide a polished end face, 36a and 38a respectively, for free space coupling of light into and out of a detector instrument (not shown) that utilizes flow cell 10.

The present invention contemplates that fluid entry segment 20 and fluid exit segment 22 may be transversely-spaced from each other along optical channel 36. The present invention further contemplates that fluid entry segment 20 and fluid exit segment 22 may be linearly-aligned across optical channel 26. In each embodiment of the present invention, fluid channel 14 intersects with optical channel 26 of the same flow cell body 12.

Major surfaces 19 and 21 further define a plurality of alignment ports 42a-b and 44a-b, respectively. The alignment ports are located to be oppositely-oriented and located on the opposed faces to aid in aligning multiple flow cells together, as will be described further hereinbelow.

The orientation of fluid entry and exit segments 20 and 22 with respect to fluid interrogation segment 24 may be selected according to the preferences of the user. For example, fluid channel 14 may take the shape of a block letter 'U', where the inlet and exit ports are defined on the same face of the flow cell, or the fluid channel may be shaped such that the inlet and exit ports are formed on adjacent faces. Additionally, the present invention contemplates that the fluid inlet and exit ports may be coaxially-aligned such that the fluid interrogation segment forms a simple intersection with optical channel 26. In each case, the optical ports are sealed by the two optical guides against fluid leakage. The interrogation beam is guided by the first optical guide, passes through the liquid flowing through the interrogation channel, and is then coupled back into the second optical guide to be captured by the detector's fiber bundle. Fluid may be directed through fluid channel 14 in the direction of arrow A. Suitable fluid conduit and connections 40 are established at the inlet and exit ports of the present invention to properly direct a fluid into and out of the flow cells of the present invention.

For example, in FIG. 3, a flow cell 40 of the present invention works by generating a flow path within a piece of a suitable polymer, e.g. COC, by means of machining or injection molding as for flow cell 10.

Flow cell 10 may also incorporate elastomeric O-rings about the optical guides so as to fluidically-seal fluid channel 14 thereat. Optical connectors 45 are attachable at faces 19 and 21 at the optical port. Optical connectors 45 each define an elongate open cable channel 47 therethrough so as to provide optical communication between an inserted cable from a detector and each of guides 36 and 38. Connectors 45 are contemplated to be attached to cell body 12 by conventional means as known in the art, including but not limited to threaded connections, adhesive connection, fasteners and the like. Additionally, fluid flow into and out of inlet and outlet ports 16 and 18, respectively, is desirably accommodated by open fluid fittings 31 and 33 positioned at each port, respectively. Fittings 31 and 33 provide connection mean for securely fastening a fluid conduit at each port or, alternatively, to attach cap seals at each port to isolate fluid channel 14.

The present invention contemplates that flow cell 10 may be manufactured by boring through cell body 12 to form optical channel 26 (including interrogation segment 24 of fluid channel 14). First and second fluid segments 20 and 22 may similarly be bored. Optical guides 36 and 38 may then be press fitted, or otherwise attached, into place. Means for attaching fittings 31 and 33 as well as for connecting optical connectors 45 to cell body 12 may also then be machined. Additionally, alignment apertures 42a-b and 46a-b may be bored as well. Alternatively, the present invention contemplates that cell body 12 may be injection molded. Optical guides 36 and 38 may then be separately inserted and emplaced. Alternatively still, optical guides 36 and 38 may be inserted into a mold prior to polymer injection, such that flow cell 10 may be formed on competion of molding.

In each such embodiment, the flow cell of the present invention is formed by suitable materials for handling radiopharmaceutical compounds. The geometry of the cells allows for different "interaction" lengths and volumes of the fluid channel allowing the simple adaptation of the design towards different radiotracer separations. The optical guides simplify the coupling of the UV light into and out of the flow cell, thereby obviating the need for complex optics. For example, the flow cell may be formed with quartz rods for the optical guides which seal the optical ports by means of a press fit, over-molding, or other low-cost manufacturing or assembly technique.

Figure 4:
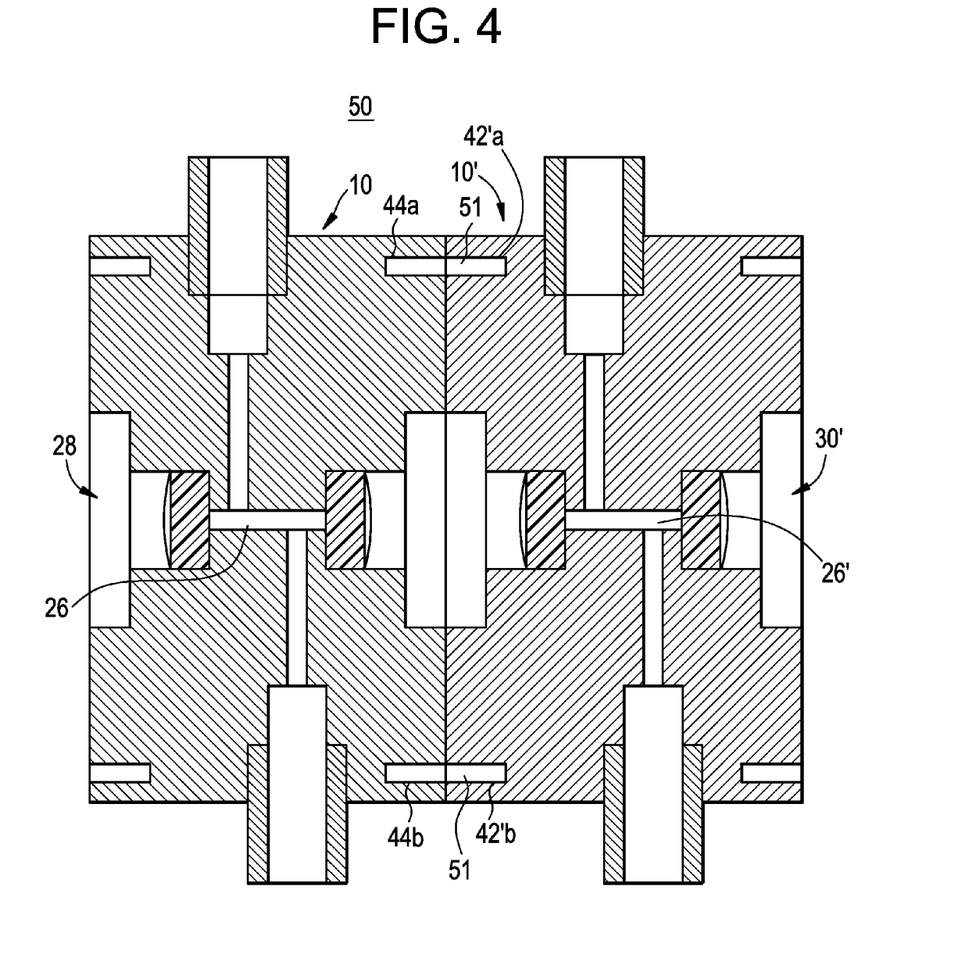
FIG. 4 depicts, in cross-section, a multi-stream optical flow cell of the present invention.
Figure 5:
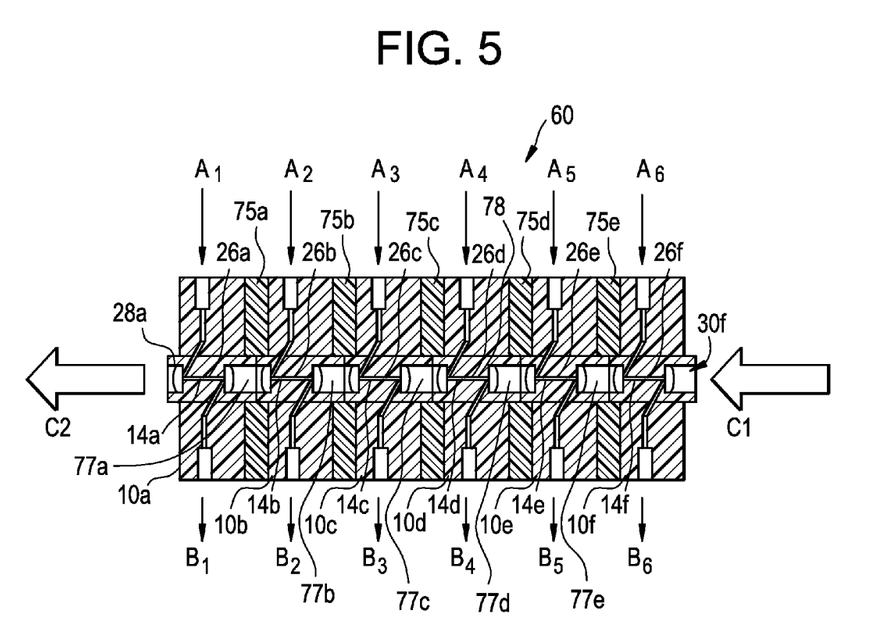
FIG. 5 depicts, in cross-section, another multi-stream optical flow cell of the present invention.

The present invention further contemplates that either optical guide could incorporate or be in the form of a lens to better focus an interrogation signal. For example, an optical guide could be shaped as a partial conical or could provide a concave or convex surface at one or both ends to account for signal diffraction entering or exiting the medium. FIGS. 3-5 depict first guide 36 having an outer convex surface 36a at one end and an opposed planar surface 36b facing interrogation channel segment 24. Second guide 38 also includes an outer concave surface 38a. Second guide 38 similarly includes a planar surface 38b in facing opposition to surface 36b of first guide 36. An interrogation beam, represented by arrows C1 and C2 in FIG. 5, may thus be more focused on the fluid passing through the interrogation channel, and/or an opposed sensor across body 12 in the opposite optical port. The present invention further contemplates that surfaces 36a, 36b, 38a, and 38b may be shaped as either convex, concave, or planar as a particular application may warrant. The present invention further contemplates that one, both, or neither of the optical guides may be provided with such a focusing shape.

FIG. 4 depicts a first embodiment of a multi-stream interrogation module 50 of the present invention. Interrogation module 50 comprises first and second flow cells 10 and 10' arrayed so that their optical channels 26 and 26', respectively, are provided in coaxial alignment so that a single interrogation beam will travel through both arrayed flow cells. Optical cables from a detector instrument would be connected at the first optical port 28 of flow cell 10 and at second optical port 30' of flow cell 10'. The alignment apertures 42a-b of flow cell 10' and 44a-b of flow cell 10 each receive linear alignment pins 51 therein so as to ensure alignment of the optical channels of the two flow cells. The present invention contemplates that other alignment mechanisms known in the art may be used to provide the proper alignment and orientation of the optical channels.

Interrogation module 50 is thus able to provide for interrogation of a fluid through two different flow cells using only a single detector instrument and interrogation beam. The present invention contemplates that only one flow cell of module 50 will be actively conducting a fluid to be interrogated in its interrogation segment 24 of its fluid channel 14. Thus, each flow cell may be dedicated to a single purification column, and each purification column may be used for the same or for different compounds.

FIG. 5 depicts another multi-stream interrogation module 60 of the present invention. Module 60 incorporates six flow cells 10a-f of the present invention such that the optical channels 26a-f of each flow cell is aligned such that a single interrogation beam may interrogate a fluid flowing through any of the fluid channels 14a-f of module 60. Module 60 includes five spacers 75a-e, each positioned between adjacent flow cells. Each Spacer 75a includes an opaque planar body defining a spacer aperture 77a-e, respectively, therethrough to accommodate the adjacent ones of optical channels 26a-e. Spacers 75a-e can provide the relative fixed engagement between flow cells 10a-f so as to maintain the desired alignment of optical channels 26a-f. Module 60 can thus be connected to six different purification columns, one per flow cell 10a-f, so that each flow cell is dedicated to the product of a particular column. The operator may decide whether the different columns are used for the same or different radiotracer. Flow of a liquid into each flow cell 10a-f is represented by arrows A1-6 at inlet ports 16a-f, respectively, while flow out of each flow cell 10a-f is represented by arrows B1-6 at outlet ports 18a-f, respectively. Arrow C1 depicts the incoming interrogation beam into optical port 30f and arrow C2 depicts the emergence of the interrogation beam out optical port 28a.

Figure 6:
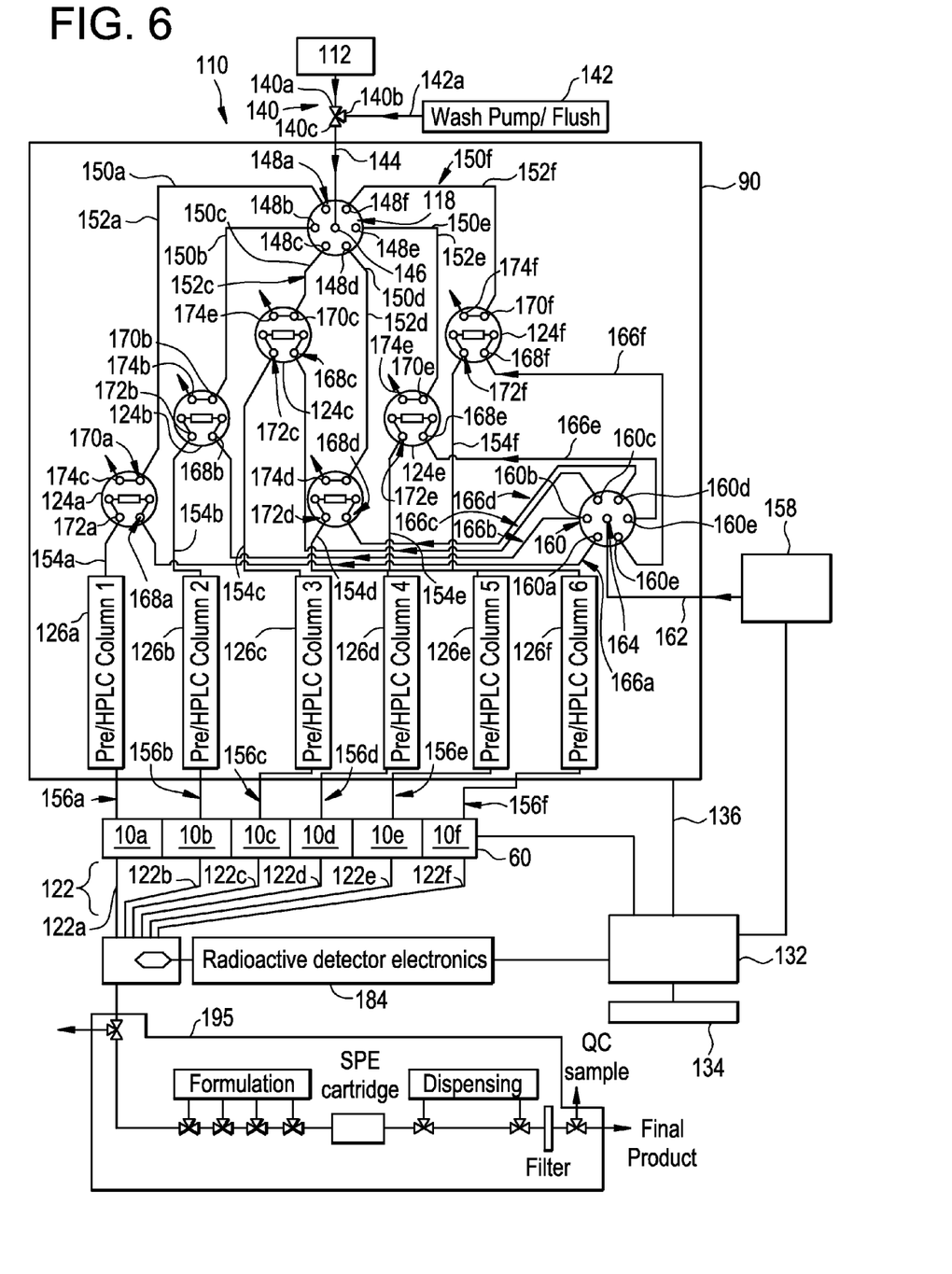
FIG. 6 depicts the connection of a multi-stream optical flow cell of the present invention to a multi-stream purification system.

FIG. 6 provides a schematic diagram of multi-stream HPLC system 110 incorporating module 60 of the present invention. The potential number of compounds that can be purified using multi-stream system 110 is determined by the selection of the multi-port valve (i.e. number of ports) 118 and the hot-cell space available for the module alongside the synthesizer itself. Commercially available hardware can be utilized for the compound dedicated inject valves 124a-f and HPLC pre/main columns 126l-f and associated tubing therefor.

Module 60 may then be connected to fluid lines at the respective exit ports 18a-f. Desirably, the fluid lines connected to exit ports 18a-f cassette based, or provided in combined array. The transfer tubes from module 60 passes through a lead shielded radiodetector housing 130. After passing through radiodetector housing 130, desirably, a fluid will be directed through a chemically inert (non-leaching) manifolds manifold to provide for either direct dispensement of the fluid or to direct the fluid for further formulation prior to dispensement.

As shown in FIG. 6, a planar base 90 supporting the valves, conduits, and columns of HPLC module 110. The interrogation module 60 need not be supported on base 90. A control system 132 provides overall control and operation of HPLC module 110, including an interactive data display 134 for displaying system and operation status but also for receiving operator input for system operation. A generic control cable 136 is shown extending from control system 132 to base 90 to indicate that control system 132 directs the operation of the valves and columns of HPLC module 110.

HPLC module 110 includes a first source valve 140 providing selective communication between the output from a tracer synthesizer 112 and a wash fluid container 142 and select valve 118. Valve 140 includes first and second input ports 140a and 140b in fluid communication with the output from synthesizer 112 and fluid container 142, respectively. The present invention contemplates that output from synthesizer 112 may be either a separate container which holds the output from synthesizer 112 or an elongate conduit directly connected to synthesizer 112 so as to provide its output to valve 140 directly. Wash fluid container 142 holds a wash/flush fluid suitable for cleaning the conduits of the dedicated components between valve 118 and module 60 so as to render them GMP-compliant for handling the output of different synthesizer batches. An elongate conduit 142a conducts the wash fluid from container 142 to port 140b of valve 140. Valve 140 also operates under the control of control system 132 so as to direct either the synthesizer output fluid or the wash fluid therethrough and out outlet port 140c, through a delivery conduit 144 to an inlet port 146 of select valve 118.

Select valve 118 is operated by control system 132 and is configured to selectably direct fluid from inlet port 146 through one of outlet ports 148a-f. Each outlet port 148a-f is connected in fluid communication with a respective fixed fluid flowpath 150a-f. Fixed fluid flowpaths 150a-f respectively include an elongate first flow conduit 152a-f, an inject valve 124a-f, an elongate second flow conduit 154a-f, and an HPLC column 126a-f. An eluate conduit 156a-f extends from each respective HPLC column 126a-f to a respective flow cell 10a-f of module 60.

HPLC module 110 includes an HPLC pump 158, operated by control system 132, for selectably directing fluid through each fixed fluid flowpath 150 and through each inject valve 124a-f to its respective HPLC column 126a-f. HPLC module 110 provides a pump valve 160, also operated by control system 132, for directing the action of pump 158 to a selected one of inject valves 124a-f. Pressure conduit 162 extends between pump 158 to an inlet port 164 of pump valve 160. Pump valve 160 is configured to selectably direct a pumping fluid from pressure conduit 162 into input port 164, through valve 160, and out through one of the pump output ports 160a-f. HPLC module 110 provides an elongate pump conduit 166a-f extending between a respective output port 160a-f of valve 160 and pump inlet port 168a-f of inject valves 124a-f.

Each inject valve 124a-f further includes a fluid inlet port 170a-f, respectively, in fluid communication with conduit 152a-f, respectively. Each inject valve 124a-f further includes a fluid outlet port 172a-f, respectively, in fluid communication with second flow conduit 154a-f, respectively. Furthermore, each inject valve 124a-f includes a sample port 174a-f for directing wash fluid from container 142 to a sample or waste container (not shown). Wash fluid directed from container 142 and out one of sample ports 174a-f may be checked for quality control to ensure that conduits 152a-f, respectively, have been cleaned to GMP standards.

Each of optical flowcells 10a-f are disconnectably connected to eluate conduits 56a-f, respectively. When any of flowcells 10a-f are disconnected from their respective eluate conduits 156a-f, the present invention contemplates that the open ends of eluate conduits 156a-f will be capped so as to seal the conduit. Unused flowcells will also be capped at the connection ports for its respective eluate conduits. Flowcell module 60 is connected to a single UV spectrometer detector 178 for interrogating fluid flowing through each flowcell. Detector 178 is operated by control system 132 which also reads and stores the data collected by detector 178. Each flowcell 10a-f thus is connected to a respective eluate conduit 156a-f at inlet port 16a-f, respectively.

HPLC module 110 additionally includes a radioactivity detector 184 which detects the activity of the fluid flowing through the portion of disposable fluid path 122 leading from flowcells 10a-f of interrogation module 60. Fluid path 122 includes six elongate hollow conduits 122a-f, one each connected to the outlet port 18a-f of module 60. Each conduit of fluid path 122 is contemplated to extend to its own valve manifold 195. For clarity, only a single manifold 195 is depicted (connected to conduit 122a). The valving and operation of manifold 195 may be controlled by control system 132, or by a separate external control system (not shown), to direct the output fluid from module 60 either directly to a dispense vial or vials, or to another system for further formulation of the fluid prior to dispensing.

While described as being formed from suitable polymers, the flow cell of the present invention may alternatively be formed using suitable metals. Whereas forming the flow cell from polymers can provide a low-cost disposable unit, forming the column from metals provides a flow cell for an interrogation module which may be cleaned, sterilized, and configured for multiple uses.

Operation:

During an analysis, it is possible that interference of the signal may occur due to the air/quartz interface of the unused cells between the source light and the detector. To minimize this, a solvent may be placed in the fluid channel 14 of the unused flow cells 10 that has a refractive index similar to that of quartz (R.I.=1.4585). Such solvents include DMSO (1.4793), Chloroform (1.4458), acetonitrile (1.3441) and water (1.3330).

Figure 7:
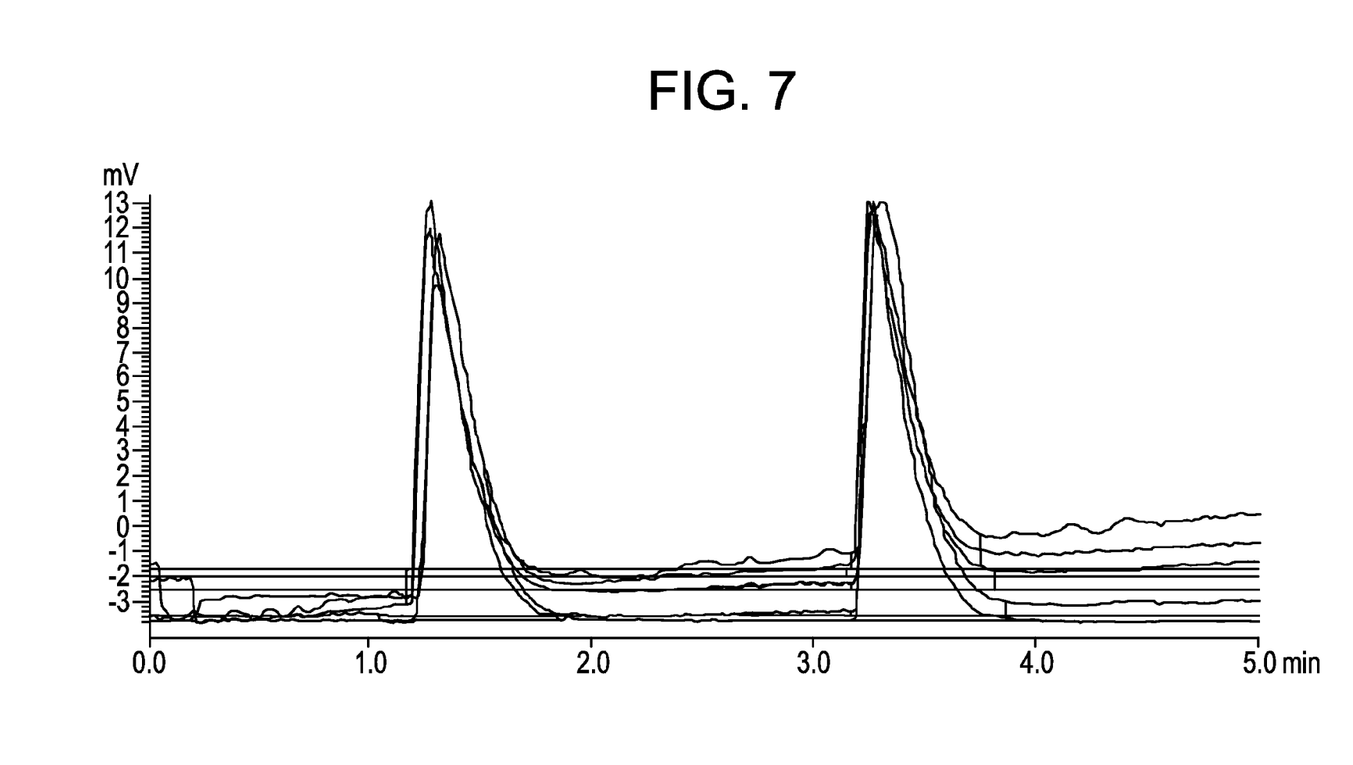
FIG. 7 depicts spectra detected using a multi-stream optical flow cell of the present invention.

Preliminary experiments indicate that refraction is not a significant problem for the system illustrated above. FIG. 7 shows five overlaid UV chromatograms consisting of a spectra obtained with a single flow cell used in the conventional manner and an array of four cells used sequentially with air or water in the unused cells. The chromatogram overlay demonstrates that any loss of signal strength or resolution is insignificant in this arrangement. Spectra were obtained at 254 nm by repeat injections of a HPLC check standard at 1 and 3 minute intervals into a water eluent at a flow rate of 1 mL$\cdot$min$^{-1}$. Peak height varies from 16 to 20 mV.

While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A multi-stream optical interrogation flow cell for a radiopharmaceutical comprising:
    a first flow cell body defining a first elongate fluid flowpath therethrough for conducting the radiopharmaceutical therethrough, said first flow cell body further defining:
    an elongate optical channel extending therethrough;
    a first and second aligned UV transparent optical guides positioned within said optical channel; and
    a first interrogation passageway of said fluid flowpath extending between said first and second optical guides such that the radiopharmaceutical flows in between the first and second optical guide;
    a second flow cell body defining a second elongate fluid flowpath therethrough for conducting the radiopharmaceutical therethrough, said second flow cell body further defining:
    an elongate optical channel extending therethrough;
    a first and second aligned UV transparent optical guides positioned within said optical channel; and
    a first interrogation passageway of said fluid flowpath extending between said first and second optical guides such that the radiopharmaceutical flows in between the first and second optical guide
    wherein said first and second optical channels are optically aligned so that a single interrogation beam is able to extend through both said optical channels;
    A first optical port and a second optical port, wherein said first optical guide seals said first optical port and said second optical guide seals said second optical port;
    A fluid inlet port and a fluid entry segment extending in fluid communication between said fluid inlet port and said interrogation passageway;
    A fluid exit port and a fluid exit segment extending in fluid communication between said fluid exit port and said interrogation passageway; and
    an opaque spacer positioned between said first and second flow cell body, wherein said spacer comprises a planar body defining an aperture therethrough in registry with said second optical port of said first flow cell body and said first optical port of said second flow cell body.

2. The optical interrogation flow cell of claim 1, wherein each said fluid inlet port and each said fluid exit port are defined by the same surface of their respective said flow cell body.

3. The optical interrogation flow cell of claim 1, wherein each said fluid inlet port and each said fluid exit port are defined by opposing surfaces of their respective said flow cell body.

4. The optical interrogation flow cell of claim 1, wherein each said fluid inlet port and each said fluid exit port are defined by non-coplanar surfaces of their respective said flow cell body.

5. The optical interrogation flow cell of claim 1, wherein each said first optical port and each said second optical port are defined by opposing surfaces of their respective said flow cell body.

6. The optical interrogation flow cell of claim 1, wherein said first and second optical guides are formed of quartz.

7. The optical interrogation flow cell of claim 1, wherein said flow cell body is formed of a polymeric material.

8. The optical interrogation flow cell of claim 1, wherein said first flow cell body is formed of stainless steel.

9. The optical interrogation flow cell of claim 1, further comprising connection and alignment mechanisms for the first and second flow cell body so as to provide each optical channel in linear-alignment for interrogation by a single interrogation beam.

10. The optical interrogation flow cell of claim 1, wherein the interrogation channel of one of the first and second interrogation flow cells holds a fluid having a similar refractive index as the material forming the optical guides where the optical channel and the flow channel intersect.

11. The optical interrogation flow cell of claim 1, wherein one of said optical guides in said first flow cell body comprises a lens.

12. The optical interrogation flow cell of claim 11, wherein said lens includes one of a planar, a convex, and a concave surface.

13. The optical interrogation flow cell of claim 12, wherein said lens is the second optical waveguide of said first flow cell body and wherein said lens includes a convex surface in facing opposition to the first optical waveguide of said second flow cell body.

14. The optical interrogation flow cell of claim 1, further comprising a third, fourth, fifth and sixth flow cell body, each of said third, fourth, fifth, and sixth flow cell bodies comprising:
    an elongate optical channel extending therethrough;
    a first and second aligned UV transparent optical guides positioned within said optical channel; and
    a first interrogation passageway of said fluid flowpath extending between said first and second optical guides such that the radiopharmaceutical flows in between the first and second optical guide
wherein said interrogation passageways of each said flow cell body are optically aligned so that a single interrogation beam is able to extend through each said interrogation passageway and provide signal information therefrom.

15. The optical interrogation flow cell of claim 14, wherein said first and sixth flow cell bodies accommodate a fitting for an optical fiber, each said fitting positioned in registry with an optical port of its respective flow cell body.

16. The optical interrogation flow cell of claim 1, wherein a portion of at least one of said first and second elongate fluid paths extend along a portion at least a portion of said interrogation passageway.

17. A multi-stream optical interrogation flow cell for a radiopharmaceutical comprising:
a plurality of flow cell bodies, each said flow cell body defining a first elongate fluid flowpath therethrough for individually conducting a radiopharmaceutical therethrough in fluid isolation from the other of said flow cell bodies, wherein each said flow cell body further defines an elongate optical channel and includes a first and second aligned optically-transparent optical guides such that the elongate fluid flowpath of each said flow cell body includes an interrogation passageway that intersects the optical channel of said flow cell body in order to direct a radiopharmaceutical flows in between the first and second optical guides, and wherein the optical channels of each of said plurality flow cell bodies are optically aligned so that a single interrogation beam is able to extend through each of the optical channels, wherein at least one waveguide further comprises a lens having a convex surface in facing opposition with a source of the interrogation beam.

18. A purification system for a radiopharmaceutical comprising a plurality of purification columns, each said purification column providing an eluate conduit to an individual one of the flow cells of an interrogation flow cell of claim 17.

* * * * *